(12) United States Patent
Schilling et al.

(10) Patent No.: US 11,521,739 B2
(45) Date of Patent: Dec. 6, 2022

(54) METHOD FOR INCLUDING REDUNDANCY IN COMMUNICATING AN ALERT CONDITION FROM AN IMPLANTED SYSTEM TO AN EXTERNAL SYSTEM

(71) Applicant: Medtronic, Inc., Minneapolis, MN (US)

(72) Inventors: Eric A. Schilling, Ham Lake, MN (US); Brian D. Kuhnley, Delano, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/140,314

(22) Filed: Jan. 4, 2021

(65) Prior Publication Data

US 2021/0257090 A1    Aug. 19, 2021

Related U.S. Application Data

(60) Provisional application No. 62/976,410, filed on Feb. 14, 2020.

(51) Int. Cl.
*G16H 40/67* (2018.01)
*A61B 5/00* (2006.01)

(52) U.S. Cl.
CPC ........... *G16H 40/67* (2018.01); *A61B 5/0004* (2013.01); *A61B 5/0015* (2013.01); *A61B 5/0031* (2013.01); *A61B 5/686* (2013.01); *A61B 5/746* (2013.01); *A61B 2560/0204* (2013.01)

(58) Field of Classification Search
CPC ...... G16H 40/67; G16H 50/20; A61B 5/0004; A61B 5/0015; A61B 5/0031; A61B 5/686; A61B 5/746; A61B 2560/0204; A61N 1/3787; A61N 1/37258
See application file for complete search history.

(56) References Cited

U.S. PATENT DOCUMENTS

| | | | |
|---|---|---|---|
| 5,713,939 | A | 2/1998 | Nedungadi et al. |
| 6,592,620 | B1 | 7/2003 | Lancisi et al. |
| 7,138,902 | B2 | 11/2006 | Menard |
| 2007/0213600 | A1 | 9/2007 | John et al. |
| 2012/0154143 | A1 | 6/2012 | DAmbrosio |
| 2015/0031938 | A1 | 1/2015 | Crosby et al. |

OTHER PUBLICATIONS

International Search Report and Written Opinion dated May 11, 2021, for corresponding International Application No. PCT/US2021/012877; International Filing Date: Jan. 11, 2021 consisting of 8-pages.

*Primary Examiner* — Nader Bolourchi
(74) *Attorney, Agent, or Firm* — Shumaker & Sieffert, P.A.

(57) ABSTRACT

A method, implantable medical system and an external system for communicating an alert signal via a transcutaneous energy transfer system (TETS), with or without the presence of transmission of the alert signal by an alternative wireless communication system, are disclosed. According to one aspect, a method in an implanted medical system includes obtaining the alert signal based on an occurrence of an event, and transmitting the alert signal from the implanted medical device to the external system via a TETS used to transfer power requests to the external system.

18 Claims, 4 Drawing Sheets

METHOD FOR INCLUDING REDUNDANCY IN COMMUNICATING AN ALERT CONDITION FROM AN IMPLANTED SYSTEM TO AN EXTERNAL SYSTEM

CROSS-REFERENCE TO RELATED APPLICATION

This application claims the benefit of U.S. Application Ser. No. 62/976410, filed Feb. 14, 2020.

FIELD

The present technology is generally related to communication between an internal implanted medical device and an external system.

BACKGROUND

Implantable medical devices may be used to monitor a patient condition and/or deliver therapy to the patient. In long term or chronic uses, implantable medical devices may include a rechargeable power source (e.g., one or more capacitors or batteries) that extends the operational life of the implantable medical device to weeks, months, or even years over a non-rechargeable device. Mechanisms are also provided to monitor operation and/or power related to such operation.

A block diagram of a system 10 that includes an implanted system 12, such as a left ventricular assist device (LVAD), and an external system 14, such as an external charging and monitoring device. There are two paths of communication between the implanted system 12 and the external system 14. One path is called a transcutaneous energy transfer system (TETS) communication path 16. This path extends between an internal TETS coil 18 and an external TETS coil 20 via inductive coupling between the TETS coils 18 and 20. Another path of communication is a wireless communication path 22, such as a Bluetooth communication path. This path extends between the transceiver 26 of the internal controller 24 of the implanted system 12 and the transceiver 30 of the external controller 28 of the external system 14.

The TETS communication path 16 carries signals from the implanted system 12 to the external system 14. The signals carried by the TETS communication path 16 request more power or less power from the external system 14, which may be provided by coupling power inductively from the external TETS coil 20 to the internal TETS coil 18. The wireless communication path 22 also carries other data signals from the implanted system 12 to the external system 14.

The signals carried by the wireless communication path 22 may include alert signals concerning operation, status and/or condition of the implanted system 12. Such alert signals may include low priority and high priority alert signals. High priority alert signals may indicate a life threatening condition that calls for urgent medical attention. The Bluetooth wireless communication technology or other radio access technology used to transmit alert signals is subject to factors that may affect successful transmission of an alert signal. These factors may include limited range, interference by signals in the environment, limited bandwidth, nulls in antenna patterns and component failure. While unsuccessful transmission of an alert signal may be mitigated by internal audible and/or vibrational alerts, communicating the reason for the alert and the action to be taken requires more than these internal alarms. Thus, reliable communication of these alert signals from the implanted system 12 to the external system 14 is desirable.

SUMMARY

The techniques of this disclosure generally relate to increasing reliability of alert signaling from an implanted medical device to an external system by redundant or alternative signaling on a TETS communication path in parallel with an alternative wireless communication system path.

Some embodiments use the communication protocol of the TETS, which is configured to provide closed loop power control, to communicate the alert signal. This may be done instead of, or in addition to, the use of an alternative wireless communication system to communicate the alert signal. In some embodiments, when the implanted medical device recognizes a fault in the alternative wireless communication system, the implanted medical device uses the TETS to transmit the alert signal instead of using the alternative wireless communication system. In some embodiments, the implantable medical device may not be able to detect a fault in the alternative wireless communication system. In such cases, the implantable medical device may transmit the alert status using the TETS in addition to attempting to transmit the alert status using the Bluetooth transmitter.

According to one aspect, a method in an implanted medical device for communicating an alert signal to an external system is provided. The method includes obtaining the alert signal based on an occurrence of an event and transmitting the alert signal from the implanted medical device to the external system via a transcutaneous energy transfer system (TETS).

According to this aspect, in some embodiments, the method includes monitoring an alternative wireless communication system configured to transmit the alert signal, and only transmitting the alert signal via the TETS when the alternative wireless communication system is in a fault condition. In some embodiments, the method includes attempting to transmit the alert signal to the external device via an alternative wireless communication system while transmitting the alert signal via the TETS. In some embodiments, transmitting the alert signal via the TETS is in response to a fault condition of an alternative wireless communication system. In some embodiments, the fault condition includes a failure of a responder of the external system to respond to one of an alert signal and a test signal. In some embodiments, the alert signal transmitted by the TETS is included in a power control signal, the power control signal having one of a request for increased power and a request for decreased power.

According to another aspect, an implanted medical device is configured to communicate an alert signal to an external system. The implanted medical device includes circuitry configured to obtain the alert signal based on an occurrence of an event, and transmit the alert signal from the implanted medical device to the external system via a transcutaneous energy transfer system (TETS).

According to this aspect, in some embodiments, the circuitry is further configured to monitor an alternative wireless communication system configured to transmit the alert signal, and only transmit the alert signal via the TETS when the alternative wireless communication system is in a fault condition. In some embodiments, the circuitry is further configured to attempt to transmit the alert signal to the external device via an alternative wireless communication system while transmitting the alert signal via the TETS. In some embodiments, transmitting the alert signal via the TETS is in response to a fault condition of an alternative wireless communication system. In some embodiments, the fault condition includes a failure of a responder of the external system to respond to one of an alert signal and a test signal. In some embodiments, the alert signal transmitted by the TETS is included in a power control signal, the power control signal having one of a request for increased power and a request for decreased power.

According to another aspect, a method in an external system in communication with an implanted medical device via a transcutaneous energy transfer system (TETS) is provided. The method includes receiving a signal via the TETS, and decoding the signal to determine a presence or absence of an alert signal.

According to this aspect, in some embodiments, the method includes transmitting via the TETS to the implanted medical device a signal responsive to a determination of the presence of the alert signal. In some embodiments, the method includes sending a fault signal to the implanted medical device when a signal from the implanted medical device sent on an alternative wireless link cannot be decoded. In some embodiments, the method further includes transmitting to the implanted medical device a signal that triggers the implanted medical device to transmit an alert signal to the external system via a selected one of the TETS and an alternative wireless communication system.

According to yet another aspect, an external system is configured to communicate with an implanted medical device via a transcutaneous energy transfer system (TETS). The external system includes circuitry configured to receive a signal via the TETS, and decode the signal to determine a presence or absence of an alert signal.

According to this aspect, in some embodiments, the circuitry is further configured to transmit via the TETS to the implanted medical device a signal responsive to the determination of the presence of the alert signal. In some embodiments, the circuitry is further configured to transmit a fault signal to the implanted medical device when a signal from the implanted medical device sent on an alternative wireless link cannot be decoded. In some embodiments, the circuitry is further configured to transmit to the implanted medical device a signal that triggers the implanted medical device to transmit an alert signal to the external system via a selected one of the TETS and an alternative wireless communication system.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, disk, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements. Thus, the functions performed by one or more of the components of the implanted medical system 34 and external system 36 may be performed by one or more processors operating according to computer instructions and/or circuitry configured to perform one or more of the functions.

Figure 1:
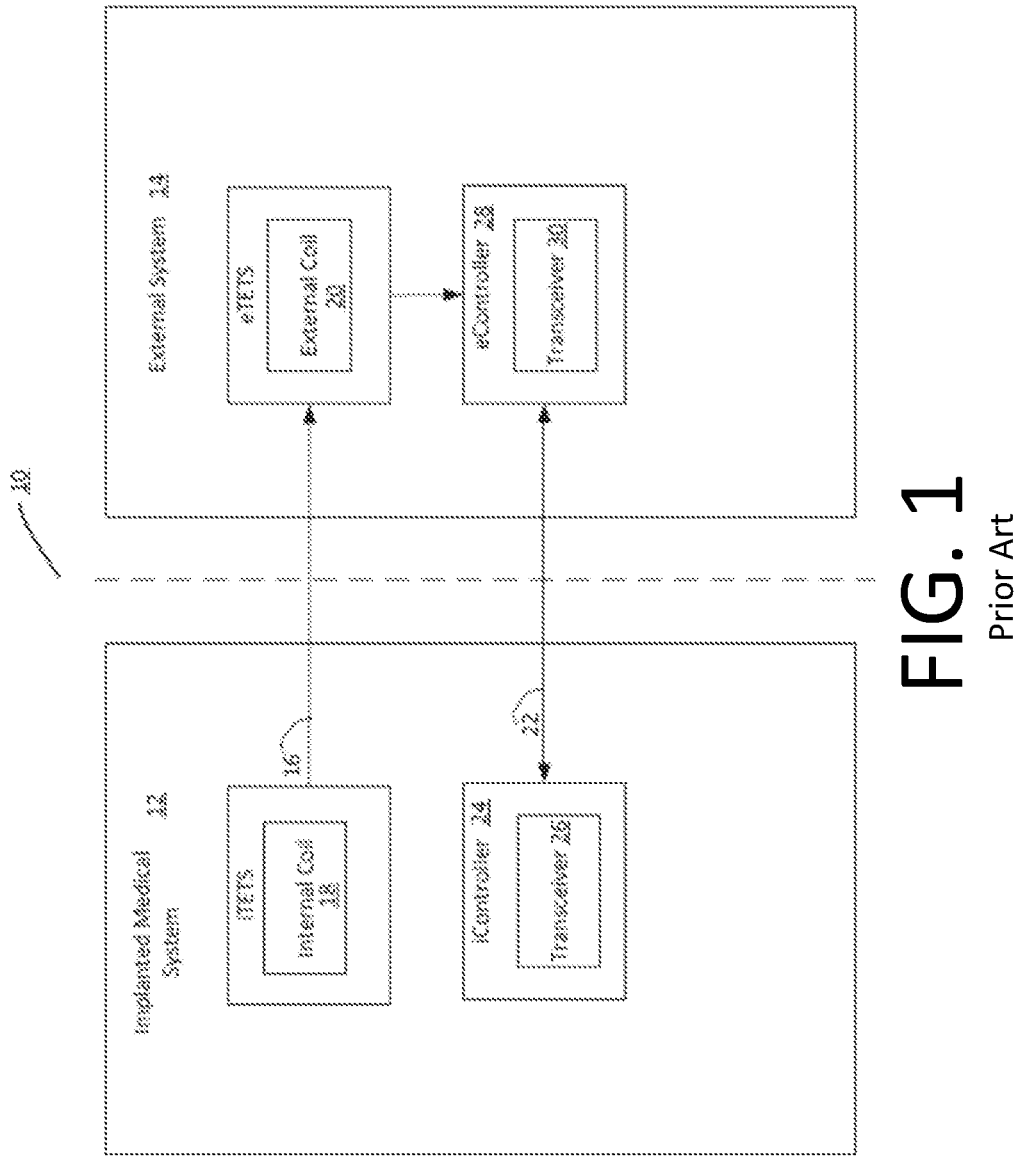
FIG. 1 is a block diagram of a known system including an implanted medical device and an external system.
Figure 2:
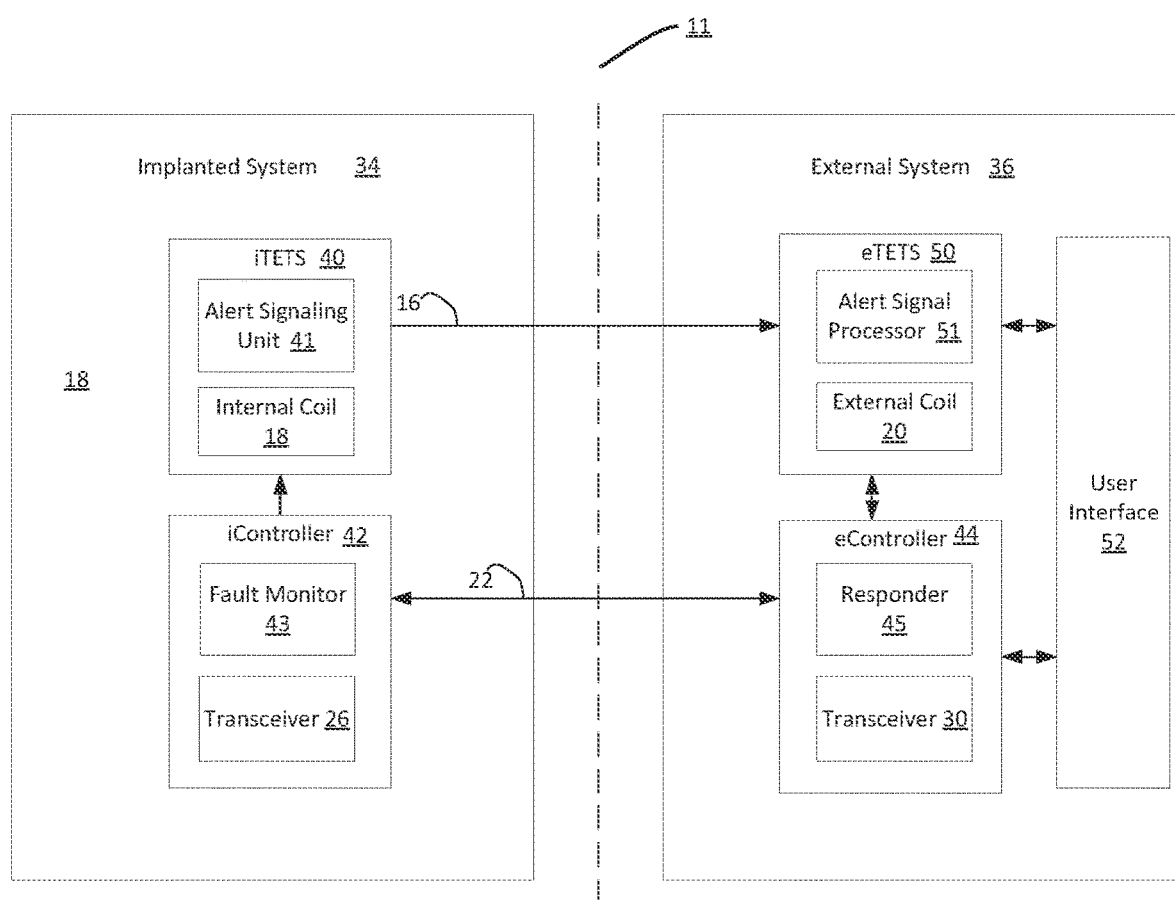
FIG. 2 is a block diagram of a system including an implanted medical device according to principles set forth herein.

FIG. 2 is a block diagram of an exemplary embodiment of a system 11 including an implanted medical system 34 and an external system 36. Similar to the known system 10 discussed above, system 11 includes the paths of communication 16 and 22. TETS communication path 16 extends from the internal TETS 40 to the external TETS 50. The internal TETS 40 has the internal coil 18 and the external TETS 50 has the external TETS coil 20. The internal TETS coil 18 may receive alert signaling from an alert signaling unit 41 of the internal TETS 40. In an alternative embodiment, the alert signaling unit 41 may be within the internal controller 42. The alert signaling unit 41 is configured to generate an alert signal which may include an indication of a cause or origin of the alert and may further include an action that when taken will resolve the cause of the alert.

The internal TETS coil 18 of the internal TETS 40 transmits the alert signal to the external TETS coil 20 of the external TETS 50. This signaling of the alert signal on the TETS communication link 16 may be instead of or in addition to sending an alert signal via the transceiver 26 of the internal controller 42. In some embodiments, the internal controller 42 may include a fault monitor 43 which may include circuitry configured to detect when transmission of an alert signal is or would be unsuccessful due to component or circuit fault and/or detect when a responder 45 of the external controller 44 fails to send an acknowledgment of successful receipt of an alert signal from the implanted medical system 34. When the fault monitor 43 detects a fault condition, the external controller 44 may send a fault signal to the internal TETS 40. Upon receipt of the fault signal by the internal TETS 40, the alert signaling unit 41 may generate and/or send an alert signal to the external system 36 via the link 16. Thus, in some embodiments, when there is an alert condition, the internal TETS 40 may send an alert signal in response to knowledge of a fault in the alternative wireless communication system (such as Bluetooth or other suitable wireless technology) that includes the transceiver 26 and transceiver 30. In some embodiments, when there is an alert condition and the internal TETS 40 is unable to learn whether there is a fault in the communication between the internal controller 42 and the external controller 44, then the internal TETS may send the alert signal in addition to or in the alternative of sending the alert signal by the alternative wireless communication system.

Thus, there are two variations of some embodiments. In one variation, the implanted medical system 34 recognizes when signaling the alert via the wireless communication path 22 is not possible or is unlikely to be successful. When an alert condition arises, the implanted medical system 34 may transmit alert status bits via the TETS communication pathway 16. In some embodiments, the internal TETS 40 monitors the alternative wireless communication system to detect when there is a fault. When a fault is detected, the implanted medical system 34 may send, via the TETS pathway 16, a signal to cause the external system 36 to produce a system replacement indicator. The system replacement indicator may indicate end of service of the battery, battery fault, critical component failure, etc. When the TETS is used, the implanted system may transmit the alert signal as bits in a sequence of bits. The external system 36 may decode these bits to determine what type of alarm to trigger and what to display to the user on a user interface 52. The user interface 52 may be a small display on a handheld device, for example. In some embodiments, the user interface 52 includes a keyboard or other text input mechanism to enable the user to input information to the external system 36. In some embodiments, the external system 36 transmit some information to the internal TETS 40.

The external TETS 50 has an alert signal processor 51 configured to receive an alert signal from the internal TETS 40. The alert signal processor 51 may process the received alert signal to determine a type of alarm to trigger in response to the alert signal and what to display on a user interface provided by the external system 36. Alternatively, some or all of the received alert signal may be processed by the external controller 44. Note that although the alert signal processor 51 is shown in the external TETS 50, the alert signal processor 51 may instead be located in the external controller 44.

In another variation, the implanted medical system 34 may be unable to recognize when alternative wireless communication system signaling is not available, is intermittent or otherwise unreliable. In such cases, the implanted medical system 34 may attempt to transmit the alert signal via of both the TETS link 16 and via the alternative wireless communication path 22, regardless of the availability of signaling via the alternative wireless communication system. In such embodiments, the external system 36 may have a mechanism to prioritize which message pathway is to trigger the alert in the event of conflicting information. The conflicting information may pertain to time stamp information, or may be used to prioritize the communication pathway, 16 or 22, in an order of perceived reliability.

Thus some embodiments, provide significant hazard mitigation by providing redundancy in alert status reporting from an implantable medical device. Such redundancy is achieved by using the TETS to communicate an alert signal instead of, or in addition to, communication of an alert signal by a Bluetooth system or other wireless communication system different from the TETS.

Note that some of the components of the external system 36 may be in more than one enclosure. For example, one external device may have the external TETS 50 whereas another external device may have the external controller 44 and user interface 52.

Figure 3:
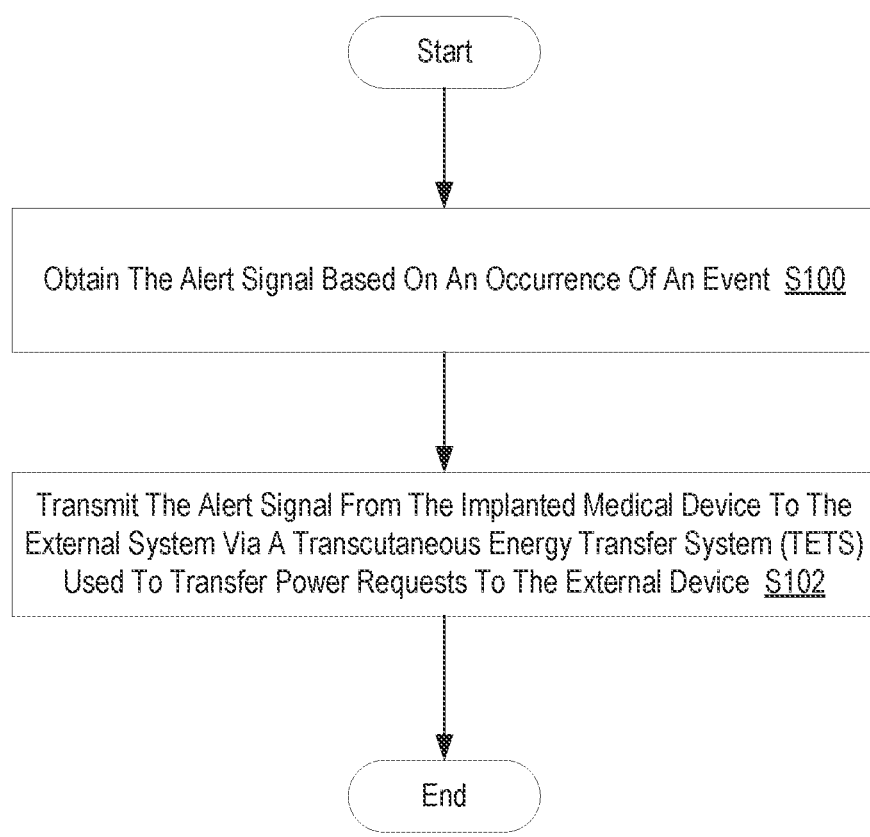
FIG. 3 is a flowchart of an exemplary process in an implantable medical system for sending an alert signal to an external system.

FIG. 3 is a flowchart of an exemplary process in an implantable medical system 34 for sending an alert signal to an external system 36. The process includes obtaining the alert signal based on an occurrence of an event (Block S100). The process also includes transmitting, via the transceiver 26, the alert signal from the implanted medical device to the external system via a TETS used to transfer power requests to the external device (Block S102). The obtaining of the alert signal may be by generating the alert signal in response to a fault condition.

Figure 4:
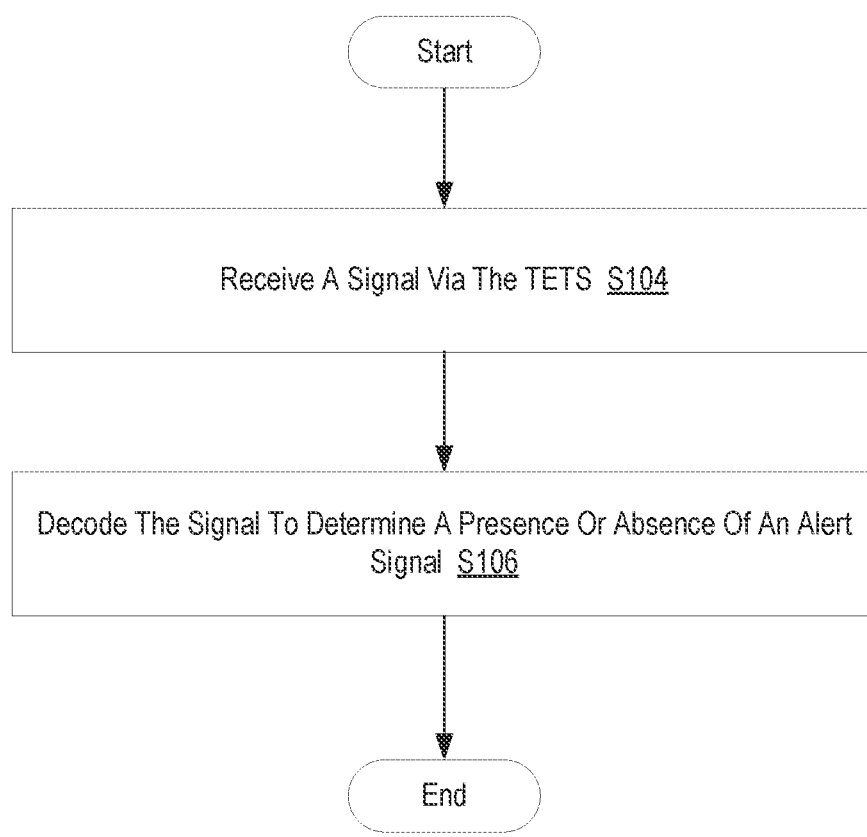
FIG. 4 is a flowchart of an exemplary process in an external system for receiving an alert signal from an implantable medical system.

FIG. 4 is a flowchart of an exemplary process in an external system 36 for receiving an alert signal from an implanted medical system 34. The process includes receiving, via the transceiver 30, a signal via the TETS (Block S104). The process also includes decoding the signal to determine a presence or absence of an alert signal (Block S106). The decoding may be by a processor or dedicated circuitry, which may be located in whole or in part in the external TETS 50 or in the external controller 44.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the following claims.

What is claimed is:

1. A method in an implanted medical system configured to communicate an alert signal to an external system, the method comprising:
   detecting an occurrence of an event;
   generating, by an alert signaling unit, the alert signal based on the occurrence of the event:
   monitoring, by an internal controller of the implanted medical system, a first wireless communication system configured to transmit the alert signal; and
   responsive to determining, by the internal controller, that the first wireless communication system is in fault condition, transmitting the alert signal from the implanted medical system to the external system via a transcutaneous energy transfer system (TETS).

2. The method of claim 1, further comprising attempting to transmit the alert signal to the external system via the first wireless communication system while transmitting the alert signal via the TETS.

3. The method of claim 1, wherein the fault condition includes a failure of a responder of the external system to respond to one of the alert signal and a test signal.

4. The method of claim 1, wherein the alert signal transmitted via the TETS is included in a power control signal, the power control signal having one of a request for increased power and a request for decreased power.

5. The method of claim 1, further comprising, producing, by the external system and based on the alert signal, a system replacement indicator.

6. An implanted medical device configured to communicate an alert signal to an external system, the implanted medical device including circuitry configured to:
  detect an occurrence of an event;
  generate, by an alert signaling unit, the alert signal based on the occurrence of the event
  monitor a first wireless communication system configured to transmit the alert signal; and
  responsive to determining that the first wireless communication system is in fault condition, transmit the alert signal from the implanted medical device to the external system via a transcutaneous energy transfer system (TETS).

7. The implanted medical device of claim 6, wherein the circuitry is further configured to attempt to transmit the alert signal to the external device via the first wireless communication system while transmitting the alert signal via the TETS.

8. The implanted medical device of claim 6, wherein the fault condition includes a failure of a responder of the external system to respond to one of the alert signal and a test signal.

9. The implanted medical device of claim 6, wherein the alert signal transmitted via the TETS is included in a power control signal, the power control signal having one of a request for increased power and a request for decreased power.

10. A method in an external system in communication with an implanted medical device via a transcutaneous energy transfer system (TETS), the method comprising:
  receiving a first signal via a first wireless communication system;
  experiencing, by a responder of the external system, a fault condition, wherein the fault condition comprises a failure of the responder to respond to the first signal;
  receiving a second signal via the TETS; and
  decoding the second signal to determine a presence or absence of an alert signal.

11. The method of claim 10, further comprising transmitting via the TETS to the implanted medical device a response signal responsive to the determination of the presence of the alert signal.

12. The method of claim 10, further comprising sending a fault signal to the implanted medical device when a signal from the implanted medical device sent on a first wireless link cannot be decoded.

13. The method of claim 10, further comprising transmitting to the implanted medical device a signal that triggers the implanted medical device to transmit the alert signal to the external system via a selected one of the TETS and the first wireless communication system.

14. An external system configured to communicate with an implanted medical device via a transcutaneous energy transfer system (TETS), the external system including circuitry configured to:
  receive a first signal via a first wireless communication system;
  experience a fault condition, wherein the fault condition comprises a failure to respond to the first signal;
  receive a second signal via the TETS; and
  decode the second signal to determine a presence or absence of an alert signal.

15. The external system of claim 14, wherein the circuitry is further configured to transmit via the TETS to the implanted medical device a response signal responsive to the determination of the presence of the alert signal.

16. The external system of claim 14, wherein the circuitry is further configured to transmit a fault signal to the implanted medical device when a signal from the implanted medical device sent on a first wireless link cannot be decoded.

17. The external system of claim 14, wherein the circuitry is further configured to transmit to the implanted medical device a signal that triggers the implanted medical device to transmit the alert signal to the external system via a selected one of the TETS and the first wireless communication system.

18. The external system of claim 14, wherein the circuitry is further configured to, responsive to determining the presence of the alert signal, produce a system replacement indicator based on the alert signal.

* * * * *